(12) United States Patent
Sato

(10) Patent No.: US 10,106,819 B2
(45) Date of Patent: Oct. 23, 2018

(54) RECOMBINANT SWINEPOX VIRUS AND VACCINES

(71) Applicant: CEVA SANTE ANIMALE, Libourne (FR)

(72) Inventor: Takanori Sato, Kanagawa (JP)

(73) Assignee: Ceva Sante Animale, Libourne (FR)

( * ) Notice: Subject to any disclaimer, the term of this patent is extended or adjusted under 35 U.S.C. 154(b) by 0 days.

(21) Appl. No.: 15/536,058

(22) PCT Filed: Dec. 18, 2015

(86) PCT No.: PCT/EP2015/080468
§ 371 (c)(1),
(2) Date: Jun. 14, 2017

(87) PCT Pub. No.: WO2016/097281
PCT Pub. Date: Jun. 23, 2016

(65) Prior Publication Data
US 2017/0335343 A1    Nov. 23, 2017

(30) Foreign Application Priority Data

Dec. 19, 2014 (EP) .................... 14307110

(51) Int. Cl.
*C12N 15/863* (2006.01)
*C12N 15/86* (2006.01)
*A61K 39/12* (2006.01)
*A61K 39/00* (2006.01)

(52) U.S. Cl.
CPC .............. *C12N 15/86* (2013.01); *A61K 39/12* (2013.01); *A61K 2039/5256* (2013.01); *A61K 2039/552* (2013.01); *C12N 2710/24043* (2013.01); *C12N 2750/10034* (2013.01)

(58) Field of Classification Search
CPC .............. A61K 2300/00; A61K 39/395; A61K 2039/505; A61K 2039/5256; A61K 39/12; A61K 2039/5254; A61K 2039/53; A61K 2039/523; C12N 2740/15062; C12N 2740/16022; C12N 2760/18351; C12N 2760/18361; C12N 2770/24322; C12N 2799/023; C12N 5/10
See application file for complete search history.

(56) References Cited

U.S. PATENT DOCUMENTS 5,651,972 A    7/1997 Moyer et al.
6,127,163 A   10/2000 Cochran et al.

OTHER PUBLICATIONS

Alfonso, et al., "The Genome of Swinepox Virus", Journal of Virology, vol. 76, No. 2, Jan. 2002, p. 783-790.
Barcena, et al., "Recombinant swinepox virus expressing β-Galactosidase: Investigation of viral host range and gene expression levels in cell culture", Virology 243, 396-405 (1998).
Foley, et al., "Swinepox virus as a vector for the delivery of immunogens", Annals of the New York Academy of Sciences, New York Academy of Sciences, vol. 64, Jan. 1, 1991, pp. 220-222.
Lin, et al., "A novel vaccine against *Streptococcus equi* ssp. *zooepidemicus* infections: The recombinant swinepox virus expressing M-like protein", Vaccine 29 (2011) 7027-7034.
Lin, et al., "Construction and immunogenicity of recombinant swinepox virus expressing capsid protein of PCV2", Vaccine 30 (2012) 6307-6313.
Lin, et al., "A novel vaccine against Porcine circovirus type 2 (PCV2) and *Streptococcus equi* ssp. *Zooepidemicus* (SEZ) co-infection", Veterinary Microbiology, 171 (2014) 198-205.
Tripathy, "Swinepox virus as a vaccine vector", Advances in Veterinary Medicine, vol. 41, Jan. 1, 1999, pp. 463-480.
Van Der Leek, et al., "Evaluation of swinepox virus as a vaccine vector in pigs using an Aujeszky's disease (pseudorabies) virus gene insert coding for glycoproteins gp50 and gp63", The Veterinary Record, 134, Jan. 1, 1994 pp. 13-18.
Winslow, et al., "Feline B7.1 and B7.2 proteins produced from swinepox virus vectors are natively processed and biologically active: Potential for use as nonchemical adjuvants", Veterinary Microbiology 111 (2005) 1-13.
Xu, et al., "Immune responses and protection efficacy of a recombinant swinepox virus expressing HA1 against swine H3N2 influenza virus in mice and pigs", Virus Research 167 (2012) 188-195.
Xu, et al., "Immune responses and protective efficacy of a recombinant swinepox virus expressing HA1 against swine H1N1 influenza virus in mice and pigs", Vaccine 30 (2012) 3119-3125.

*Primary Examiner* — Bao Q Li
(74) *Attorney, Agent, or Firm* — Cesari and McKenna, LLP

(57) ABSTRACT

The present invention relates to novel recombinant swinepox viruses and their use in vaccine compositions. The recombinant swinepox viruses of the invention are produced 5 by inserting one or more foreign genes into IL-18 binding protein (IL18bp) gene of swinepox virus. The invention is particularly suited to produce swine vaccines, particularly for vaccinating swine against PCV2 infection.

Figure 2:
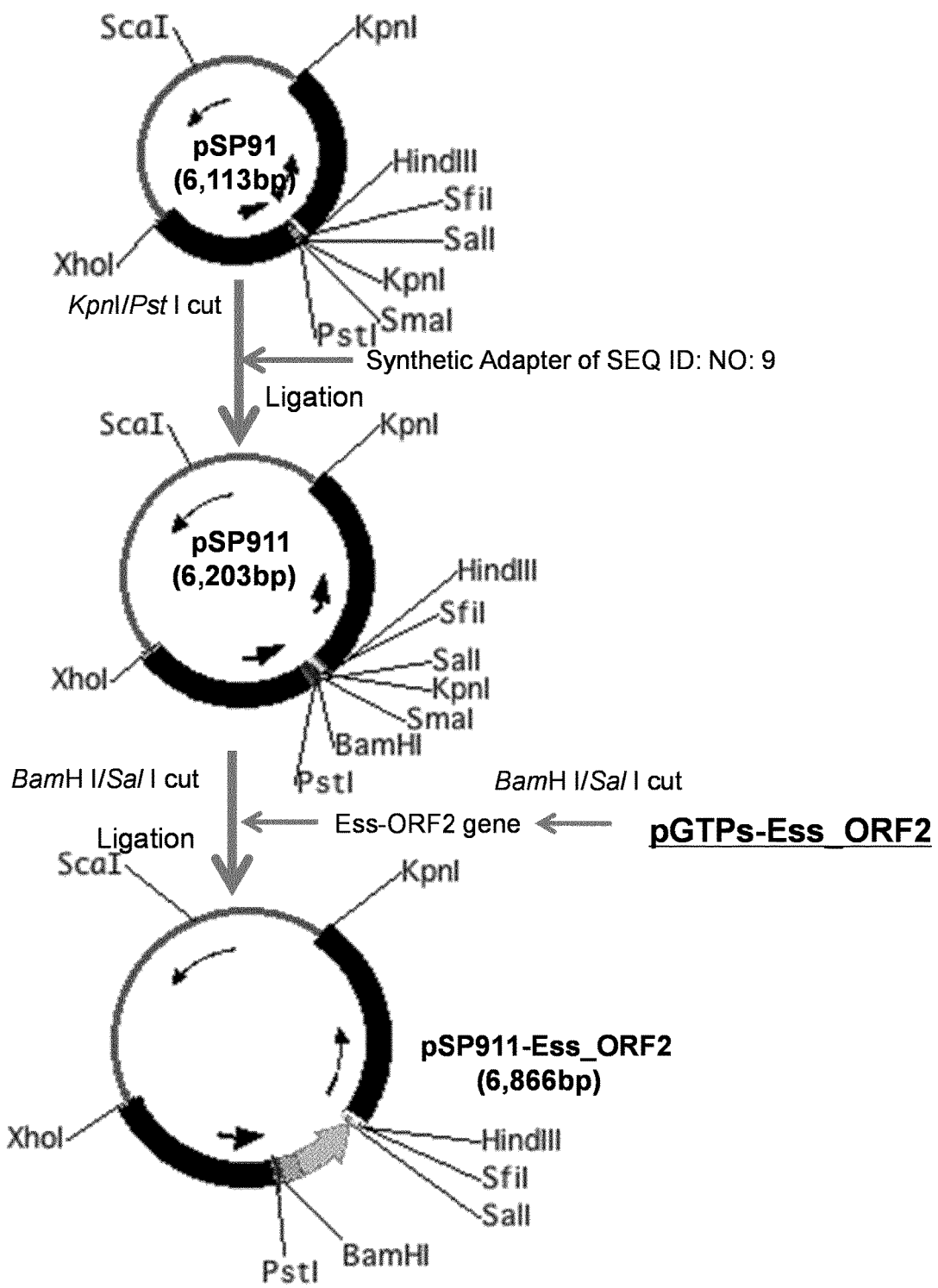

22 Claims, 6 Drawing Sheets
Specification includes a Sequence Listing.

Fig. 1

RECOMBINANT SWINEPOX VIRUS AND VACCINES

CROSS REFERENCE TO RELATED APPLICATIONS

This application is the National Stage of International Application No. PCT/EP2015/080468, filed on Dec. 18, 2015, which claims the benefit of European Application No. 14307110.8, filed on Dec. 19, 2014. The contents of both applications are hereby incorporated by reference in their entirety.

The present invention relates to novel recombinant swinepox viruses and their use in vaccine compositions. The recombinant swinepox viruses of the invention are produced by inserting one or more foreign genes into IL-18 binding protein (IL18bp) gene of swinepox virus. The invention is particularly suited to produce swine vaccines, particularly for vaccinating swine against PCV2 infection.

BACKGROUND

Different types of viruses have been proposed in the art as vector for gene delivery or peptide expression in vivo. In particular, veterinary vaccines have been prepared that express at least one relevant antigen using recombinant viruses such as poxviruses (Ogawa R. et al., Vaccine, 8:486-490 (1990)), adenoviruses (HSU, K. H. et al., Vaccine, 12; 607-612 (1994)), baculoviruses, as well as herpesviruses (Shin, M.-F. et al., Proc. Natl. Acad. Sci. U.S.A., 81:5867-5870 (1984)). Examples of specific virus vectors that permit the expression of a gene for a foreign antigen include Aujeszky's disease virus (pseudorabies virus; PRV) (Van Zijl M. et al., J. Virol., 65:2761-2765 (1991)), herpesvirus of turkey (HVT) (Morgan R. W. et al., Avian Dis. 36:858-870 (1992)), and Marek's disease virus (MDV). Recombinant vectors based on the genus herpesvirus are under intensive study.

There is, however, a need in the art for new viral vector products that can be used to express recombinant peptides or proteins in vivo. In this regard, poxviruses have been engineered to encode different polypeptides. Poxviruses, once released into the blood from infected cells, can infect other cells and thereby potentially lead to elevated expression levels. Recombinant poxviruses have been produced from different types of poxviruses, including cowpox virus, vaccinia virus, and swinepox virus (SPV). So far, however, SPV recombinants have been produced essentially by cloning foreign gene sequences in a genetic region that is considered non-essential for survival of SPV, the TK region (Richard W. Moyer, Eladio Vinuela, E. P. J. Gibbs, U.S. Pat. No. 5,651,972 (1997)).

The inventors of the present invention have now found and validated a novel gene insertion region of SPV into which a variety of foreign gene sequences can be inserted. The resulting recombinant SPV viruses allow efficient and stable expression of the cloned gene sequence, and have large cloning capacity. Furthermore, these viruses have improved immunogenicity in vivo and can be used to produce therapeutics or vaccines for treatment of any mammal, particularly in swine.

SUMMARY OF THE INVENTION

The present invention relates to novel recombinant swinepox viruses and their use for gene delivery and expression in vivo, particularly in vaccine compositions. The recombinant swinepox viruses of the invention contain one or more foreign gene sequences into IL-18 binding protein (IL18bp) gene of swinepox virus. The invention is particularly suited to produce swine vaccines, particularly for vaccinating swine against PCV2 infection.

A first object of the present invention thus relates to a recombinant swinepox virus (rSPV) comprising at least one first foreign gene sequence in its genome, wherein said first foreign gene sequence is inserted into the IL18bp gene of the rSPV genome. In a particular embodiment, the foreign gene sequence is inserted in replacement of all or part of the viral IL18bp gene sequence. In a further particular embodiment, the rSPV of the invention further comprises at least a second foreign gene sequence inserted in a distinct region of the rSPV genome, for instance into the viral Thymidine kinase (TK) gene or Ankyrin repeat protein gene.

A further object of the invention resides in a nucleic acid molecule comprising the genome of a rSPV as defined above.

A further object of the invention is a host cell comprising a rSPV or a nucleic acid molecule of the invention.

The present invention further provides a method for producing a rSPV, comprising infecting or introducing into a competent cell a nucleic acid molecule as defined above and collecting the rSPV.

The invention also relates to a method for propagating a rSPV, comprising infecting a competent cell a rSPV as defined above and collecting the rSPV produced by said cells.

The invention also concerns a composition, preferably a veterinary composition, comprising a rSPV as defined above, or a cell as defined above, or a nucleic acid molecule as defined above, and an excipient.

A further object of the invention is a vaccine composition comprising a rSPV as defined above, or a cell as defined above, or a nucleic acid molecule as defined above, a suitable excipient and, optionally, an adjuvant.

The invention also relates to a rSPV or cell or nucleic acid molecule as defined above for use for delivering a therapeutic or vaccinating peptide or protein to a porcine.

The invention also relates to a rSPV or cell or nucleic acid molecule as defined above for use for immunizing or vaccinating a porcine against a pathogen.

The invention also concerns a vaccination kit for immunizing a porcine which comprises the following components:
  a. an effective amount of a rSPV or vaccine as defined above, and
  b. a means for administering said rSPV or vaccine to said porcine.

A further object of the invention relates to a shuttle plasmid or vector comprising a transgene flanked by two nucleic acid sequences homologous to IL18bp gene sequence, said flanking sequences allowing homologous recombination between the shuttle plasmid and a SPV genome.

The invention may be used to deliver and express any foreign gene sequence to a mammal, particularly a porcine. It is particularly suited for expressing foreign antigens to immunize or vaccinate porcine (e.g., pigs, piglets, sow).

LEGEND TO THE FIGURES

Figure 1:
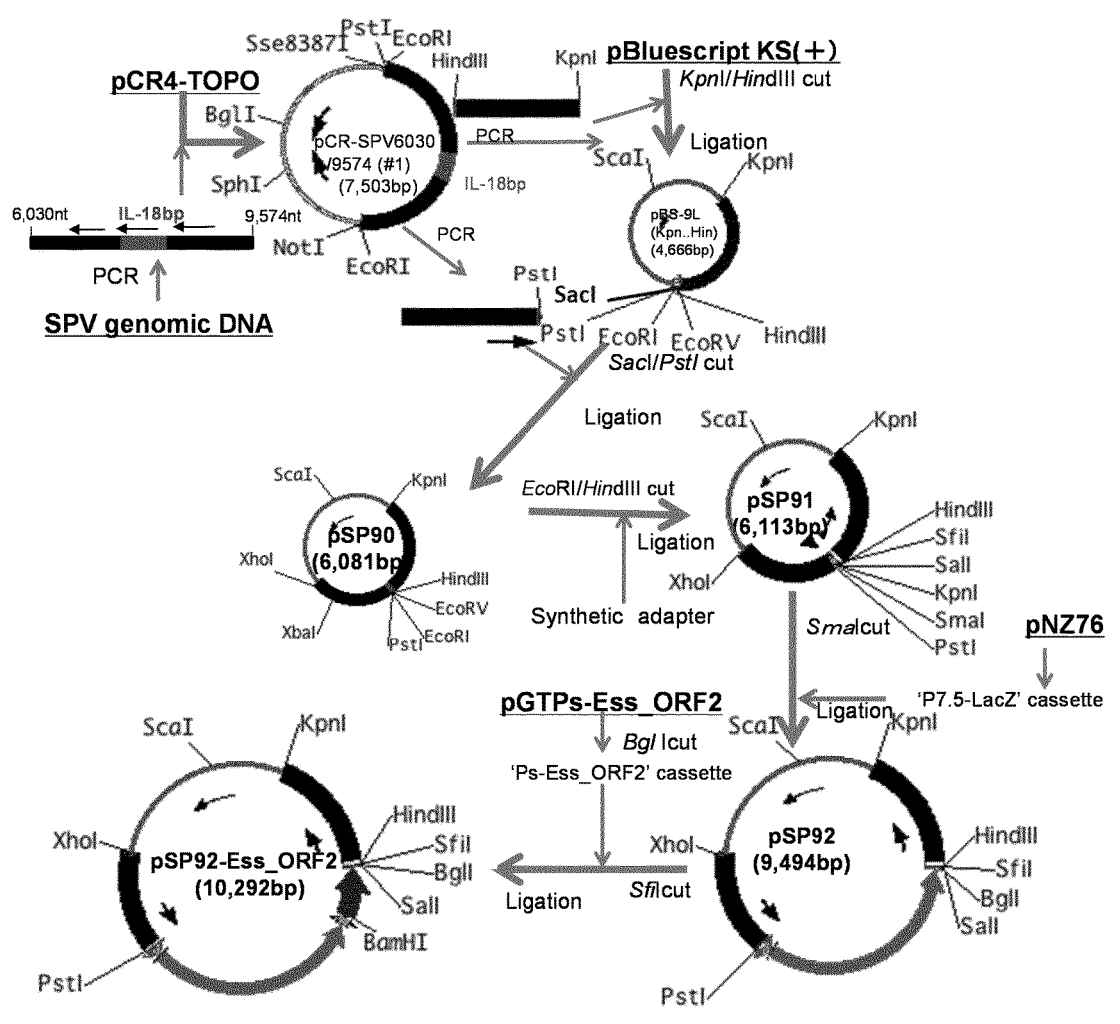

FIG. 1. Construction of homologous plasmid pSP92-Ess_ORF2.

FIG. 2. Construction of homologous plasmid pSP911-Ess_ORF2.

Figure 3:
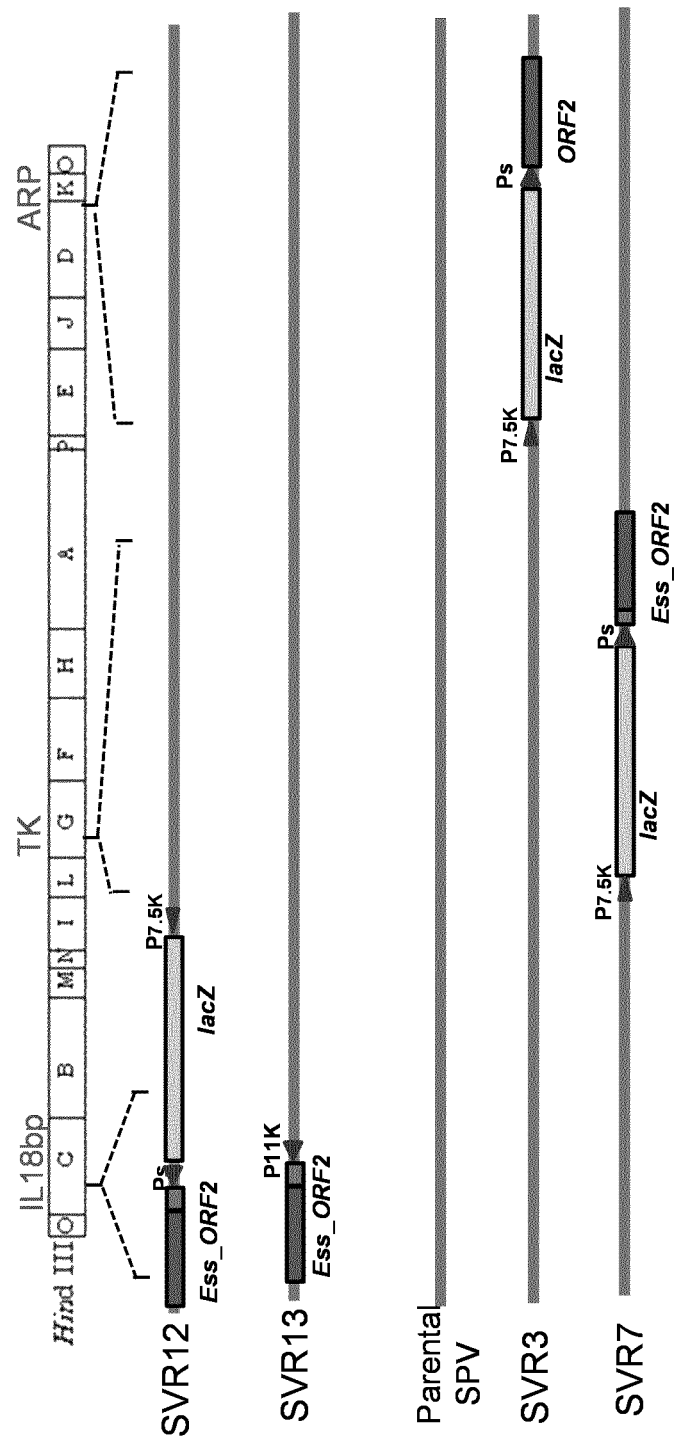

FIG. 3. Illustration of genome structures of parental and recombinant SPVs.

Figure 4:
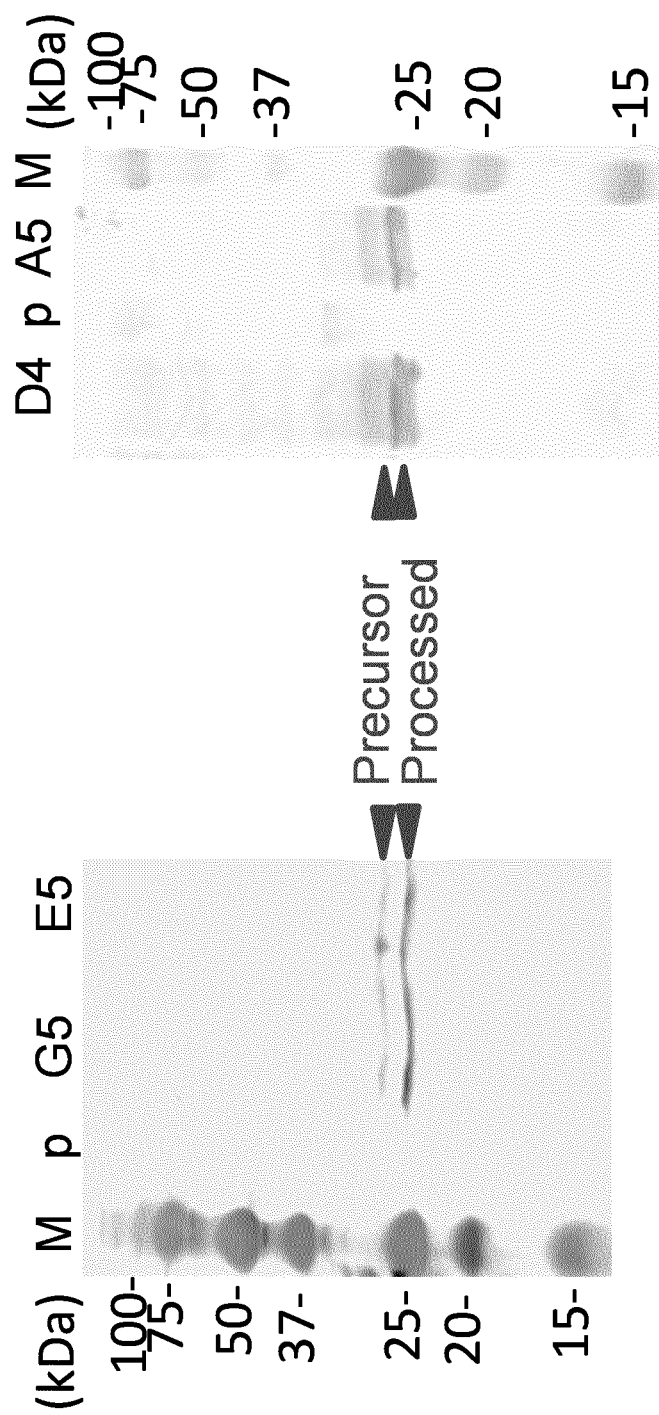

FIG. 4. Western blotting of purified SVR12 and SVR13. ESK-4 cells were infected with parental SPV (p), SVR12 clone 1H2C9D4G5 (G5) or clone 2F5D5E5 (E5), or SVR13 clone G2C2D4 (D4), or clone D10E5A5 (A5). Six days later, cell lysates were applied to 15% SDS-PAGE and western blot analysis using rat anti-ORF2 (1:500), biotin conjugated goat anti-rat IgG secondary (1:1000), and ABC-ALP (Vecterstain). M: Molecular weight marker.

Figure 5:
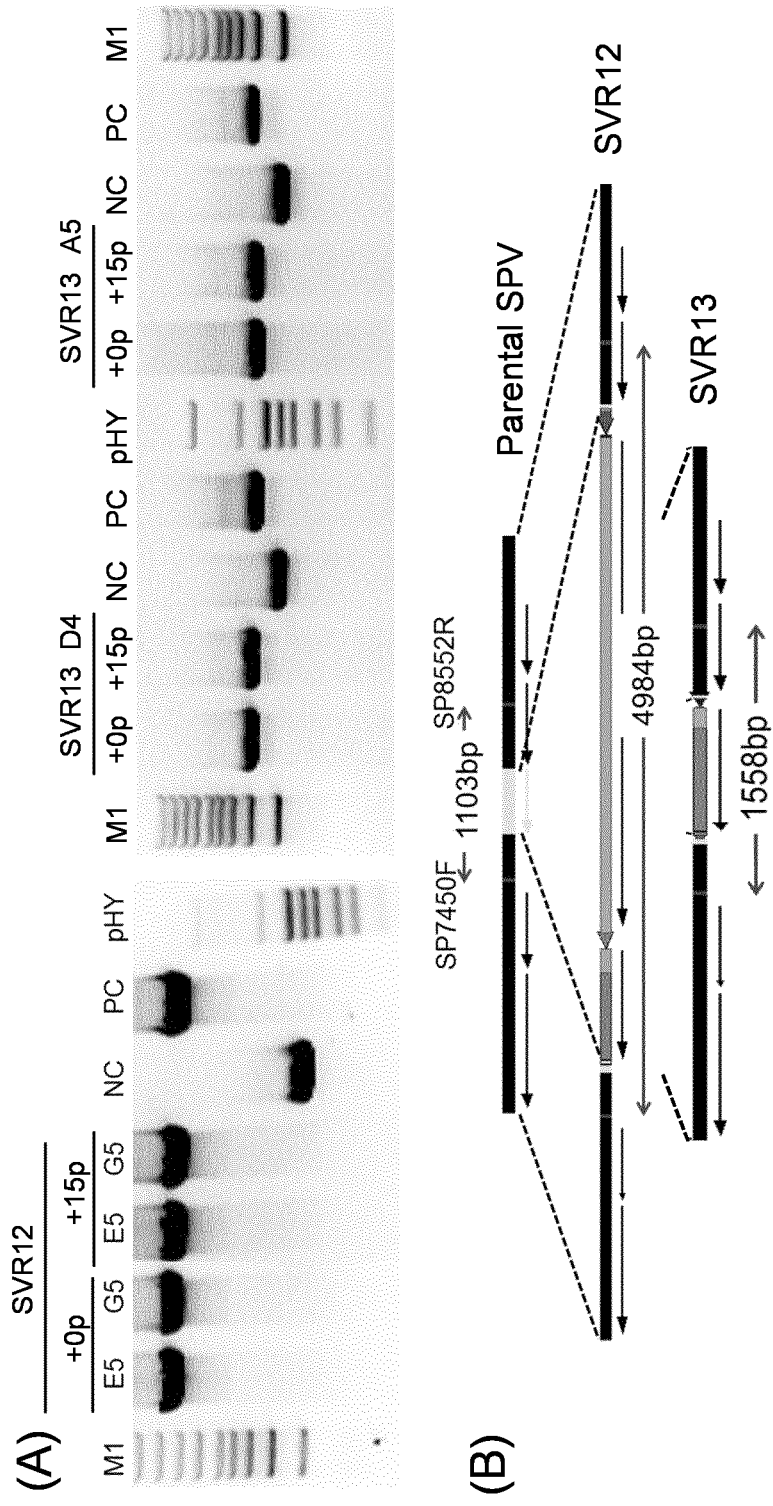

FIG. 5. PCR check of rSPVs in vitro passage.

(A) PCR results: PCR was conducted using a primer set of SP7450F and SP8552R. Each template was virus DNA of in vitro passage +0 or +15p of SVR12 clone 1H2C7F3E5 (E5), clone 2F5D5E5G5 (G5), and SVR13 clone G2C2D4 (D4), or clone D10E5A5 (A5). Each transfer plasmid at transfection for making SVR12 or SVR13, and pCR4-SPV6030/9574, was used for a template of positive control (PC) or negative control (NC), respectively. Molecular weight markers were 10 kb (M1) and pHY. (B) IL-18bp flanking regions of parent and rSPVs. Yellow box is IL-18bp gene.

Figure 6:
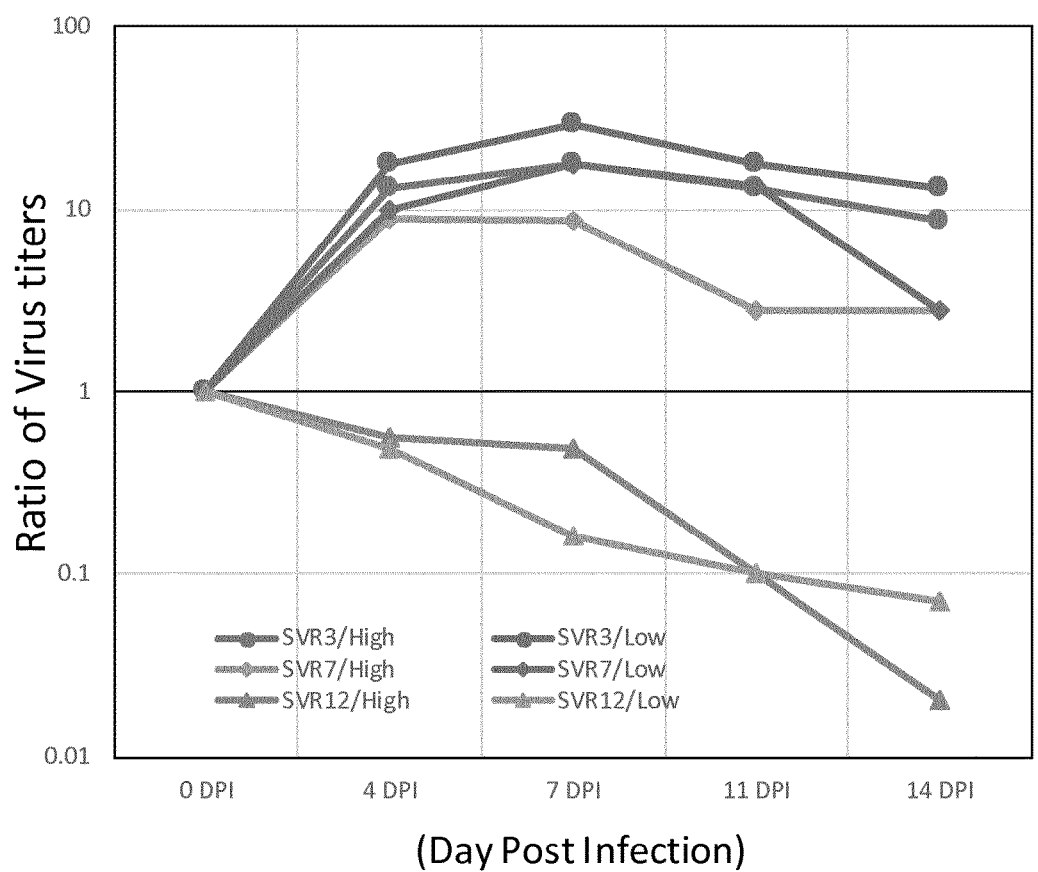

FIG. 6. Relative growth of rSPVs in Vero cells.

Vero cells in 6-well plates were infected with each of three kinds of recombinant SPVs, SVR3, SVR7 or SVR12, at high (about 0.01) or low (about 0.001) MOI. At 0, 4, 7, 11 and 14 days post infection (DPI), each infected cells and supernatants were harvested with cell scrapers, and freeze and thawed. For virus titration, these cell lysates after centrifuged were diluted serially, and infected into ESK-4 cells and incubated at 37° C. for 1week to form plaques. Relative growth ratios were calculated on the basis of each titer of 0 DPI.

DETAILED DESCRIPTION OF THE INVENTION

The present invention relates to the novel recombinant swinepox viruses and the uses thereof. The recombinant swinepox viruses of the invention contain one or more foreign gene sequences into IL-18 binding protein (IL18bp) gene of swinepox virus. As shown in the experimental section, such novel SPV vectors allow sustained and efficient gene expression. Furthermore, the rSPVs of the invention are stable and can produce improved immune responses in vivo. Moreover, surprisingly, SPV vectors of the invention are safer than previous SPVs since they do not grow in mammalian cells such as Vero cells. This is the first report of a SPV virus containing a deleted IL18-bp gene, and the first demonstration that foreign gene sequences may be cloned in this site resulting in stable, immunogenic and highly-producing recombinant SPV vectors. The rSPV of the invention may further contain more than one foreign gene sequences, inserted into the same or distinct locations. They may be used alone or in combination with other recombinant viruses or antigens to generate improved vaccines. The invention is particularly suited to produce swine vaccines, particularly for vaccinating swine against PCV2 infection.

rSPVs

Within the context of the invention, a recombinant swinepox virus designates, generally, a swinepox virus having an artificially (e.g., recombinantly) engineered genome. rSPV include, particularly, swinepox viruses containing foreign genetic material or sequence in their genome. rSPV typically comprise a SPV genome containing a foreign genetic sequence, packaged into a SPV capsid or envelop, which may also contain a foreign protein or peptide.

rSPV of the present invention may be prepared starting from any SPV, such as any naturally occurring SPVs or any SPVs available from collections such as ATCC, CNCM, etc. Preferably, the rSPV of the invention are produced from SPV kasza strain (VR-363), isolate 17077-99 (GeneBank Acc: AF410153.1), or strain VTCC/AVA/121 (GeneBank Acc: KJ725378.1). Such SPVs are available from collections or libraries, or may be cloned from their publicly available genomic sequences. Further SPV isolates may also be isolated from infected animals and used to prepare rSPV of the invention.

SPV or rSPV may be cultured or maintained or propagated in any suitable cell. For instance, SPVs may be cultured, maintained or propagated in embryonic swine kidney cells, such as ESK-4 cells (CL-184), routinely cultured at 37.0 in 5% CO2 in Ham's F-12K medium (Gibco, Cat. No.: 21127-022) supplemented with 1% streptomycin-penicillin (Gibco, Cat. No.: 15140-122) and 5% FBS (Gibco, Cat. No.: 10437-028).

In order to construct a recombinant virus of the present invention, initially, the SPV virus may be propagated in a suitable host cell and then the genomic DNA obtained. Subsequently, the IL18bp region of the genomic DNA is identified, optionally deleted, in all or in part, and a foreign gene sequence (or a cloning site allowing insertion of a foreign gene sequence) is inserted into the region, optionally in replacement of all or part of the endogenous IL18bp gene sequence. The recombinant SPV genome thus obtained may be used to produce rSPV by transformation of suitable competent cells according to conventional techniques. Alternatively, a shuttle vector may be produced containing a foreign gene sequence (or a cloning site) flanked by sequences homologous to IL18bp gene regions. Upon introduction into a competent cell in the presence of a SPV virus or genome, homologous recombination between the shuttle vector and the genome generates the rSPV. Of course, once a rSPV has been engineered as described above, it can be easily replicated and propagated by simple culture on any competent cells.

SPVs may be cultured, maintained or propagated in embryonic swine kidney cells, such as ESK-4 cells (CL-184), routinely cultured at 37.0 in 5% CO2 in Ham's F-12K medium (Gibco, Cat. No.: 21127-022) supplemented with 1% streptomycin-penicillin (Gibco, Cat. No.: 15140-122) and 5% FBS (Gibco, Cat. No.: 10437-028). DNA can be extracted from virus-infected cells according to any conventional method. For instance, cells grown in monolayers can be scraped and then spun to harvest the supernatant. After protein is denatured in a lysis buffer and removed, DNA can be extracted with phenol and/or ethanol.

The IL18bp gene of a viral SPV DNA contains approximately 402 bp, and is generally located at nt residues 7745-8146 of SVP genome. As a specific example, in SPV kasza strain (VR-363), the IL18bp gene is located at nt7745-8146.

In a particular embodiment, the rSPVs of the invention contain a foreign gene sequence inserted at a location between nt 7750 and nt 8140 of a SPV genome. Insertion of the foreign gene sequence causes an interruption of the native IL18bp gene sequence, generally preventing expression of a functional IL18bp. In a preferred embodiment, the foreign gene sequence is inserted in replacement of IL18bp gene sequence. In this regard, preferred rSPVs of the invention comprise a deletion of from at least 10 to approximately 400 nt of the genomic IL18bp gene sequence, and a foreign gene sequence located in place of the deleted sequence.

Preferred rSPVs of the invention comprise a foreign gene sequence contained in the IL18bp gene, wherein the endogenous IL18bp gene lacks at least 50 nt, preferably at least 100 nt, even more preferably at least 150 nt, at least 200 nt, at least 250 nt, at least 300 nt, further more preferably between 320 nt and 380 nt.

Specific and preferred rSPVs of the invention contain a deletion of at least nt 100-200 of IL18bp gene, even more preferably of at least nt50-300 of IL18bp gene, such as nt19-369 of IL18bp gene.

The construction of a rSPV of the invention may be carried out using methods known per se in the art, following guidance and information contained in the present application. In particular, the skilled artisan can insert a foreign gene sequence in the IL18bp sequence, in replacement or all or part of the endogenous sequence, by using known methods such as mutagenesis, PCR, homologous recombination, etc.

In a particular embodiment, a shuttle vector is prepared by recombinant DNA technology in which a foreign gene sequence is cloned flanked by two IL18bp homology regions. The homology regions typically contain each between 50-1000 nt of IL18bp gene sequence, allowing specific homologous recombination. The shuttle vector may be prepared from any known or conventional plasmids, cosmids, phages, and the like, such as pBS plasmids, pBR322, pUC18, pUC19 and pHC79. The shuttle plasmid may then be introduced into an SPV-infected cell using known techniques such as electroporation, calcium phosphate, a lipofectin-based method, or the like. Recombinant SPV viruses having integrated the foreign gene sequence are then selected. Their sequence can be verified. The rSPV can then be maintained in any suitable competent cell. The virus can be maintained in culture, or purified and frozen or lyophilized.

Foreign Gene Sequence

The foreign gene sequence may be any nucleic acid sequence or molecule not naturally present in a SPV genome, or not naturally present at such a location in a SPV genome. A foreign gene sequence typically comprises a nucleic acid sequence encoding an mRNA, a peptide or a polypeptide (or protein). The foreign gene sequence may, for instance, encode various types of active molecules, such as an antigen, adjuvant, cytokine, lymphokine, growth factor, enzyme, label, etc.

In a preferred embodiment, the foreign gene sequence encodes an antigen (peptide, polypeptide or protein antigen) from a pathogen of a porcine infectious disease, and most preferably an antigen from a virus, bacterium, fungus, or protozoa. Within the context of the invention, a peptide typically designates a molecule comprising from 4 to 30 amino acids. A polypeptide is any amino acid polymer comprising more than 30 amino acids. The term polypeptide includes full length proteins.

The foreign gene sequence preferably encodes a peptide or polypeptide (e.g., glycoprotein, capsid protein, or fragment thereof) of a virus or pathogen selected from porcine circovirus (PCV1, PCV2, PCV2A, PCV2B), *Actinobacillus pleuropneumonia*; Adenovirus; Alphavirus such as Eastern equine encephalomyelitis viruses; *Balantidium coli*; *Bordetella bronchiseptica*; *Brachyspira* spp., preferably *B. hyodyentheriae*, *B. pilosicoli*, *B. innocens*, *Brucella suis*, preferably biovars 1, 2 and 3; Classical swine fever virus, African swine fever virus; *Chlamydia* and *Chlamydophila* sp. and preferably *C. pecorum* and *C. abortus*; *Clostridium* spp., preferably *Cl. difficile*, *Cl. perfringens* types A, B and C, *Cl. novyi*, *Cl. septicum*, *Cl. tetani*; Digestive and respiratory Coronavirus; *Cryptosporidium parvum*; *Eimeria* spp; *Eperythrozoonis suis* currently named *Mycoplasma haemosuis*; *Erysipelothrix rhusiopathiae*; *Escherichia coli*; *Haemophilus parasuis*, preferably subtypes 1, 7 and 14; Hemagglutinating encephalomyelitis virus; lsospora suis; Japanese Encephalitis virus; *Lawsonia intracellulars*; *Leptospira* spp., preferably *Leptospira australis*, *Leptospira canicola*, *Leptospira grippotyphosa*, *Leptospira icterohaemorrhagicae*, *Leptospira interrogans*, *Leptospira Pomona* and *Leptospira tarassovi*; *Mannheimia haemolytica*; *Mycobacterium* spp. preferably, *M. avium*, *M. intracellular* and *M. bovis*: *Mycoplasma hyponeumoniae*; *Parvovirus*; *Pasteurella multocida*; Porcine cytomegolovirus; Porcine parovirus; Porcine reproductive and respiratory syndrome virus: Pseudorabies virus; Rotavirus; Sagiyama virus; *Salmonella* spp. preferably, *S. thyhimurium* and *S. choleraesuis*; *Staphylococcus* spp. preferably, *S. hyicus*; *Streptococcus* spp., preferably Strep, suis; Swine cytomegalovirus; Swine herpes virus; Swine influenza virus; Swinepox virus; *Toxoplasma gondii*; Vesicular stomatitis virus or virus of exanthema of swine.

In a particularly preferred embodiment, the foreign gene sequence encodes a PCV2 antigen, particularly a PCV2 protein or peptide, even more particularly a PCV2 capsid (e.g., ORF2) protein or peptide.

The foreign gene sequence may contain a transcriptional promoter to allow or increase expression of the encoded mRNA or polypeptide. The promoter used may be a synthetic or natural promoter, including a SPV promoter, a poxvirus promoter, or a promoter derived from different viruses or cells such as promoters derived from eukaryotic or prokaryotic organisms. Specific examples of promoters include the vaccinia virus 7.5-kD promoter (P7.5k) (Davison A. J. et al., J. Mol. Biol., 210(4):749-69 (1989)), 11-kD promoter (P11k) (Bertholet et al., Proc. Nat. Acad. Sci., 82:2096-2100 (1985)) or 28-kD promoter (P28k) (Weir J. P. & Moss B., J. Virol. 61:75-80 (1987)), or an artificial synthetic Poxvirus promoter (Ps), the thymidine kinase promoter of herpesvirus (Ross L. J., Gen. Virol. 74:371-377 (1993)), gB protein promoter (supra) of HVT or MDV, the IE promoter of human cytomegalovirus (HCMV) (Alting-Mess M. A., Nucleic Acids Res., 17:9494 (1989)), SV40 promoter (Gunning P., Proc. Natl. Acad. Sci., 84:4931-4835 (1987)), [beta] actin promoter (supra, and Kost A. T., Nucleic Acids Res., 11:8287-8301 (1983)), [beta]-globin promoter (Spitzner J. R., Nucleic Acids Res., 18:1-11 (1990)), the LTR promoter of Rous sarcoma virus (Fiek A. et al., Nucleic Acids Res., 20:1785 (1992)), and the like. In addition, promoters of the structural proteins or the essential genes of SPV can also be used.

rSPV of the invention may contain several foreign gene sequences, located in a same cloning region (i.e., IL18bp) and/or in distinct cloning sites (one of them being IL18bp). In a particular embodiment, the rSPV of the invention comprises at least 2 foreign gene sequences encoding two distinct antigens (from a same or distinct pathogen). In a further particular embodiment, the rSPV of the invention comprises at least a foreign gene sequence encoding a PCV2 antigen and a foreign gene sequence encoding a distinct antigen. In another particular embodiment, the rSPV of the invention comprises a foreign gene sequence encoding an antigen and a foreign gene sequence encoding an adjuvant or a cytokine. In such multivalent rSPV of the invention, the at least two foreign gene sequences may be under the control of the same or distinct promoter, and in the same or opposite orientation.

Nucleic Acid Molecules

The invention also relates to nucleic acid molecules comprising the genome of a rSPV of the invention. Nucleic acid molecules of the invention may be DNA or RNA, double-stranded or single-stranded. Single-stranded DNA or RNA may be the coding strand, also known as the sense strand, or it may be the non-coding strand, also referred to as the anti-sense strand. The invention also relates to variants or analogs of such nucleic acid molecules, e.g., molecules having at least 85%, 90%, 95%, 96%, 97%, 98% or more sequence identity thereof.

The degree of homology between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 5371 1) (Needleman, S.

B. and Wunsch, CD., (1970), Journal of Molecular Biology, 48, 443-453). Using GAP with the following settings for DNA sequence comparison: GAP creation penalty of 5. 0 and GAP extension penalty of 0.3. Nucleic acid molecules may be aligned to each other using the Pileup alignment software, available as part of the GCG program package, using, for instance, the default settings of gap creation penalty of 5 and gap width penalty of 0.3.

Suitable experimental conditions for determining whether a given nucleic acid molecule hybridizes to a specified nucleic acid may involve pre-soaking of a filter containing a relevant sample of the nucleic acid to be examined in 5×SSC for 10 minutes, and pre-hybridization of the filter in a solution of 5×SSC, 5×Denhardt's solution, 0.5% SDS and 100 [mu]g/ml of denatured sonicated salmon sperm DNA, followed by hybridization in the same solution containing a concentration of 10 ng/ml of a P-dCTP-labeled probe for 12 hours at approximately 45<0>C, in accordance with the hybridization methods as described in Sambrook et al. (1989; Molecular Cloning, A Laboratory Manual, 2nd edition, Cold Spring Harbour, N.Y.). The filter is then washed twice for 30 minutes in 2×SSC, 0.5% SDS at least 55<0>C (low stringency), at least 60<0>C (medium stringency), at least 65<0>C (medium/high stringency), at least 70<0>C (high stringency), or at least 75<0>C (very high stringency). Hybridization may be detected by exposure of the filter to an x-ray film.

The nucleic acid molecules according to the invention may be provided in the form of a nucleic acid molecule per se such as naked nucleic acid molecules; a vector; virus or host cell etc. Vectors include expression vectors that contain a nucleic acid molecule of the invention.

Host Cells

In a further embodiment of the invention, there is provided a host cell transformed with a nucleic acid or with a rSPV according to the invention. Such cells can produce rSPVs of the invention. Suitable examples of host cells are known to those skilled in the art or can be readily selected by those skilled in the art. Host cells are preferably eukaryotic cells such as mammalian (e.g., pig), fungal (e.g. *Saccharomyces cerevisiae, pichia, aspergillus, fusarium*), insect and plant cells. Specific examples of host cells are swine kidney cells, such as ESK-4 cells (CL-184).

Vaccine Compositions and Methods

The term "vaccine" as used herein includes any composition which may be used to cause, stimulate or amplify an immune response in an animal (e.g., pigs) against a pathogen. Particular examples of vaccines of the invention are composition able to cause or stimulate or amplify immunity against a PCV2 virus. In a vaccine of the invention, the at least one foreign gene sequence shall encode an antigen or an adjuvant.

The term "immunization" includes the process of delivering an immunogen to a subject. Immunization may, for example, enable a continuing high level of antibody and/or cellular response in which T-lymphocytes can kill or suppress the pathogen in the immunized non-human animal, such as pig, which is directed against a pathogen or antigen to which the animal has been previously exposed.

Vaccines of the invention comprise an immunologically effective amount of a rSPV or nucleic acid or cell as described above in a pharmaceutically acceptable vehicle.

In practice, the exact amount required for an immunologically effective dose may vary from subject to subject depending on factors such as the age and general condition of the subject, the nature of the formulation and the mode of administration. Appropriate "effective amount" may be determined by one of ordinary skill in the art using only routine experimentation. For instance, methods are known in the art for determining or titrating suitable dosages of a vaccine to find minimal effective dosages based on the weight of the non-human animal subject, concentration of the vaccine and other typical factors. In a typical embodiment, the vaccine comprises a unitary dose of between 10 and 10,000,000 $TCID_{50}$, preferably between 100 and 1,000,000 $TCID_{50}$, even more preferably of between 1,000 and 100,000 $TCID_{50}$, of a rSPV of the invention. $TCID_{50}$ designates the median tissue culture infective dose, i.e., the amount of virus that produces pathological change in 50% of inoculated cell cultures.

The dosage of the vaccine, concentration of components therein and timing of administering the vaccine, which elicit a suitable immune response, can be determined by methods such as by antibody titrations of sera, e.g., by ELISA and/or seroneutralization assay analysis and/or by vaccination challenge evaluation.

Vaccines may comprise other ingredients, known per se by one of ordinary skill in the art, such as pharmaceutically acceptable carriers, excipients, diluents, adjuvants, freeze drying stabilizers, wetting or emulsifying agents, pH buffering agents, gelling or viscosity enhancing additives, or preservatives, depending on the route of administration.

Examples of pharmaceutically acceptable carriers, excipients or diluents include, but are not limited to demineralised or distilled water; saline solution; vegetable based oils such as peanut oil, arachis oil, safflower oil, olive oil, cottonseed oil, maize oil, sesame oil, or coconut oil; silicone oils, including polysiloxanes, such as methyl polysiloxane, phenyl polysiloxane and methylphenyl polysolpoxane; volatile silicones; mineral oils such as light liquid paraffin oil, or heavy liquid paraffin oil; squalene; cellulose derivatives such as methyl cellulose, ethyl cellulose, carboxymethylcellulose, carboxymethylcellulose sodium salt, or hydroxypropyl methylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Examples of adjuvants include, but are not limited to, oil in water emulsions, aluminum hydroxide (alum), immunostimulating complexes, non-ionic block polymers or copolymers, cytokines (like IL-1, IL-2, IL-7, IFN-[alpha], IFN-[beta], IFN-y, etc.), saponins, monophosphoryl lipid A (MLA), muramyl dipeptides (MDP) and the like. Other suitable adjuvants include, for example, aluminum potassium sulfate, heat-labile or heat-stable enterotoxin(s) isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

Examples of freeze-drying stabilizer may be for example carbohydrates such as sorbitol, mannitol, starch, sucrose, dextran or glucose, proteins such as albumin or casein, and derivatives thereof.

Vaccines may comprise antigens from several pathogens, such as PCV2, *Actinobacillus* pleuropneunomia; Adenovirus; Alphavirus such as Eastern equine encephalomyelitis viruses; *Balantidium coli; Bordetella bronchiseptica; Brachyspira* spp., preferably *B. hyodyentheriae, B. pilosi-* coli, *B. innocens, Brucella suis*, preferably biovars 1, 2 and 3; Classical swine fever virus, African swine fever virus; *Chlamydia* and *Chlamydophila* sp. and preferably *C. pecorum* and *C. abortus; Clostridium* spp., preferably *Cl. difficile, Cl. perfringens* types A, B and C, *Cl. novyi, Cl. septicum, Cl. tetani*; Digestive and respiratory Coronavirus; *Cryptosporidium parvum; Eimeria* spp; *Eperythrozoonis suis* currently named *Mycoplasma haemosuis; Erysipelothrix rhusiopathiae; Escherichia coli; Haemophilus parasuis*, preferably subtypes 1, 7 and 14; Hemagglutinating encephalomyelitis virus; lsospora suis; Japanese Encephalitis virus; *Lawsonia intracellulars; Leptospira* spp., preferably *Leptospira australis, Leptospira canicola, Leptospira grippotyphosa, Leptospira icterohaemorrhagicae, Leptospira interrogans, Leptospira Pomona* and *Leptospira tarassovi; Mannheimia haemolytica; Mycobacterium* spp. preferably, *M. avium, M. intracellular* and *M. bovis: Mycoplasma hyponeumoniae*; Parvovirus; *Pasteurella multocida*; Porcine cytomegolovirus; Porcine parovirus, Porcine reproductive and respiratory syndrome virus: Pseudorabies virus; Rotavirus; Sagiyama virus; *Salmonella* spp. preferably, *S. thyhimurium* and *S. choleraesuis; Staphylococcus* spp. preferably, *S. hyicus; Streptococcus* spp., preferably Strep, suis; Swine cytomegalovirus; Swine herpes virus; Swine influenza virus; Swinepox virus; *Toxoplasma gondii*; Vesicular stomatitis virus and/or virus of exanthema of swine.

The vaccine compositions of the invention may be liquid formulations such as an aqueous solution, water-in-oil or oil-in-water emulsion, syrup, an elixir, a tincture, a preparation for parenteral, subcutaneous, intradermal, intramuscular or intravenous administration (e.g., injectable administration), such as sterile suspensions or emulsions. Such formulations are known in the art and are typically prepared by dissolution of the antigen and other typical additives in the appropriate carrier or solvent systems. Liquid formulations also may include suspensions and emulsions that contain suspending or emulsifying agents.

The route of administration can be percutaneous, via mucosal administration, or via a parenteral route (intradermal, intramuscular, subcutaneous, intravenous, or intraperitoneal). The vaccine of the invention can conveniently be administered intranasally, transdermally (i.e., applied on or at the skin surface for systemic absorption), parenterally, ocularly, etc. The parenteral route of administration includes, but is not limited to, intramuscular, intravenous, intraperitoneal routes and the like.

The vaccines of the invention can be administered as single doses or in repeated doses. The vaccines of the invention can be administered alone, or can be administered simultaneously or sequentially administered with one or more further compositions, such as for example other porcine immunogenic or vaccine compositions. Where the compositions are administered at different times the administrations may be separate from one another or overlapping in time.

The present invention also relates to methods of immunizing or inducing an immune response in a non-human mammal (e.g., pigs) comprising administering to said mammal a rSPV or a nucleic acid, or a cell or a vaccine as described above.

Vaccines of the invention are preferably administered to pigs, adult pigs, but also to young pigs, piglets or to pregnant sow. Vaccination of pregnant sows is advantageous as it can confer passive immunity to the newborns via the transmission of maternal antibodies. The pigs may be less than 7, 6, 5, 4, 3, 2 or 1 week old; 1 to 6 weeks old; 2 to 5 weeks old; or 3 to 4 weeks old. Desirably, the vaccine is administered to a subject who has not yet been exposed to the pathogen.

The present invention also provides a container comprising an immunologically effective amount a rSPV, nucleic acid, cell or vaccine as described above. The invention also provides vaccination kits comprising an optionally sterile container comprising an immunologically effective amount of the vaccine, means for administering the vaccine to animals, and optionally an instruction manual including information for the administration of the immunologically effective amount the composition for treating and/or preventing infectious disease.

PCV2 Vaccine

The invention is particularly suited for the treatment (preventive curative) of PCV2 infection and associated diseases.

Currently developed PCV2 vaccines, such as Circovac® (Merial), Ingelvac®, CircoFLEX (Boehringer lngelheim Vetmedica), or Suvaxyn®, are either inactivated PCV2 vaccines or Sub-Unit vaccines. PCV2 Sub-Unit vaccines typically use a purified, recombinant PCV2A capsid protein produced by recombinant expression of the ORF2 gene of PCV2A. In this regard, the protein encoded by ORF2 of PCV2 isolates Imp1011 has been reported in EP1741785. A protein encoded by ORF2 of PCV2 isolate PCV2Rm has been reported in WO2010/061000. The protein encoded by ORF2 of PCV2 isolate 412 has been reported in EP1816200. Another protein encoded by an ORF2 of a further PCV2 isolate has been reported in EP1036180 or EP2225367. Improved synthetic ORF2-type proteins have been described in WO2013/030320 and in WO2014/167060.

In a particular embodiment, the present invention relates to a rSPV as defined above wherein the foreign gene sequence encodes a PCV2 antigen, more preferably a PCV2 protein, polypeptide or peptide. In a more preferred embodiment, the present invention relates to a rSPV as defined above wherein the foreign gene sequence encodes a PCV2 ORF2 polypeptide or a fragment thereof. In a particular embodiment, the ORF2 is selected from ORF2 of PCV2 isolates Imp1011, PCV2Rm, or 412, or a ORF2 having at least 80% sequence identity to such proteins, or an immunogenic fragment thereof comprising at least 10, 15, more preferably at least 20 contiguous amino acid residues thereof.

A further aspect of the invention relates to methods of treating and/or preventing a PCV2 associated disease in a non-human mammal, and to methods of immunizing or vaccinating a non-human animal subject, such as pigs, swine, sow, piglet, against PCV2 infection, comprising administering to said animal subject a rSPV, a nucleic acid, a cell, or vaccine composition as defined above.

PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exsudative epidermitis, necrotizing lymphadenitis, and congenital tremors. Preferably, a non-human animal subject, such as pig, is protected to an extent in which one to all of the adverse physiological symptoms or effects of PCV2 infections are significantly reduced, ameliorated or totally prevented.

In one embodiment, the vaccine compositions of the invention are administered to a pig susceptible to or otherwise at risk for PCV2 infection to enhance the subject own immune response capabilities.

Preferably, the subject is a pig which is in need of vaccination against Postweaning Multisystemic Wasting Syndrome (PMWS) and/or Porcine Dermatitis and Nephropathy Syndrome (PDNS).

Further aspects and advantages of the invention shall be disclosed in the following experimental section, which illustrates the claimed invention.

EXAMPLES

Example 1: Construction of Plasmids for Making Recombinant SPVs (1) Constructing pSP92-Ess_ORF2 (FIG. 1)

The SPV genomic DNA was prepared as follows:

SPV kasza strain (VR-363) and embryonic swine kidney cell, ESK-4 cells (CL-184) could be purchased from the American Type Culture Collection (ATCC). The ESK-4 cells were routinely cultured at 37.0 in 5% CO2 in Ham's F-12K medium (Gibco, Cat. No.: 21127-022) supplemented with 1% streptomycin-penicillin (Gibco, Cat. No.: 15140-122) and 5% FBS (Gibco, Cat. No.: 10437-028). For SPV genomic DNA preparation, confluent ESK-4 cells in a 225 cm2 flask were infected with SPV and incubated for 6 days until the cells were showing 100% cytopathic effect (CPE). The infected cells were then harvested by scraping the cells into the medium and centrifuging at 1300 rpm for 5 min. The medium was decanted, and the cell pellet was gently resuspended in 2 ml Phosphate Buffer Saline (PBS: 1.5 g Na2HPO4, 0.2 g KH2PO4, 0.8 g NaCl and 0.2 g KCl per litter H$_2$O) and subjected to two successive freeze-thaws. Cellular debris was then removed by centrifuging at 3000 rpm for 5 min at 4° C. SPV virions, present in supernatant, were then pelleted by centrifugation at 20,000×g for 20 min at 4° C. The resultant pellet was then suspended with 10 mM Tris pH7.5. SPV genomic DNAs were then extracted from the SPV virions by suspending with the lysis buffer (20 mM Tris, pH9, 0.1M NaCl2, 5 mM EDTA, 0.1% SDS, 0.2 mg/ml proteinase K) and incubating at 60.0 for 5 min. Phenol:chloroform (1:1) extraction was conducted two times, and the sample precipitated by the addition of two volumes of ethanol and centrifugation. The supernatant was decanted, and the pellet (SPV DNA) was air dried and rehydrated in 10 mM Tris pH7.5, 1 mM EDTA at 4° C.

The flanking regions of interleukin 18 binding protein (IL-18bp) gene in the SPV genome were cloned by Polymerase Chain Reaction (PCR). Two primers (synthetic oligonucleotides), SP6030F and SP9574R shown in SEQ ID NOs: 1 and 2 were purchased from Takara Bio. PCR reaction was conducted using LA Taq polymerase (Takara Bio) and a primer set of SP6030F and SP9574R with SPV DNA as a template according to the producer's protocol.

```
SEQ ID NO: 1:
CGAATTCATTCCTTTATCTTTA

SEQ ID NO: 2:
GGAACTACGTTATACGATCAT
```

The amplified DNA of about 3.5 kbp was confirmed by a 0.8% agarose gel electrophoresis, and purified from the gel using the QIAquick Gel Extraction Kit (Qiagen). The purified DNA fragment was cloned into pCR4-TOPO vector (Invitrogen) according to the producer's protocol. 12 white ampicillin-resistant transformants were picked up and grown in LB broth containing 50 micro-g/ml ampicillin, and each plasmid was prepared with QuickLyse Miniprep Kit (Qiagen). Each plasmid was digested with ScaI, and two kinds of candidate plasmids (both directions of inserted DNA) were selected. The inserted DNAs of them were sequenced with Dye Terminator Cycle Sequencing reagent (DTCS) and CEQ2000XL sequencer (Beckman Coulter). One of the candidate plasmids, pCR-SPV6030/9574 (#1), was confirmed that it contained the DNA fragment from 6,030 nt to 9,574 nt of SPV genomic DNA (GeneBank Acc: NC_003389) and used as a basic plasmid (FIG. 1).

Next, PCR mutagenesis was conducted to delete a part of the IL-18bp gene and to introduce the multiple restriction enzyme sites using pCR-SPV6030/9574 (#1) as a template and using two kinds of primer sets, (1) SEQ ID NOs: 3 and 4 or (2) SEQ ID NOs: 5 and 6.

```
SEQ ID NO: 3:
TTCGCCCTTACGGTACCATTCCTTTATCTTTATAAACG

SEQ ID NO: 4:
CTATAATATTAAATAAGCTTTATGGAGTTGTTTAAATAC

SEQ ID NO: 5:
CACACGATAACACTGCAGTCCACATATTACGGTTC

SEQ ID NO: 6:
GCCGCGAATTCGCCCTCGAGGAGCTCACTACG
```

Each PCR products were applied to a 0.8% agarose gel electrophoresis and purified using the QIAquick Gel Extraction Kit. The purified DNA fragment, which was amplified by PCR using a primer set of SEQ ID NOs: 3 and 4, was digested with two restriction enzymes, KpnI and HindIII, and ligated with the same restriction enzymes-cut-pBluescript KS(+) (Stratagene). The resulted plasmid pBS-9L (Kpn ... Hin) (FIG. 1) was digested with SacI and PstI, and the same restriction enzymes-cut DNA fragment amplified by PCR using a primer set of SEQ ID NOs: 5 and 6, was inserted into it. The resulting plasmid was named as pSP90 (FIG. 1).

Between EcoRI and HindIII sites in the multi-restriction enzyme sites of pSP90 were replaced with the oligonucleotide adapter prepared by annealing two synthetic DNA oligonucleotides of SEQ ID NOs: 7 and 8. The resulting plasmid was named as pSP91 (FIG. 1).

```
SEQ ID NO: 7:
AATTGCCCGGGTACCGTCGATCGACTTTTTATGGCCCCCCCGGCCA

SEQ ID NO: 8:
AGCTTGGCCGGGGGGGCCATAAAAAGTCGATCGACGGTACCCGGGC
```

The DNA fragment of 'P7.5 promoter-LacZ' gene cassette derived from pNZ76, which was cut with HindIII and SmaI of pNZ76 and followed by blunting by DNA polymerase (described in the U.S. Pat. No. 5,387,519) was ligated into SmaI site of pSP91. The resulting plasmid was named as pSP92 (FIG. 1), and 'P7.5-LacZ' gene cassette was inserted into the IL-18bp gene (from 8,146 nt to 7,745 nt in the SPV genome).

The 0.8 kb BglI-cut-fragment derived from pGTPs-Ess_ORF2 (Example 1 of WO2014/167060) was inserted into SfiI site of pSP92, and the resulting plasmid was named as pSP92-Ess_ORF2 (FIG. 1). This plasmid included the 'strong poxvirus promoter (Ps)-Ess_ORF2 (modified PCV2-ORF2)' gene cassette also within the IL-18 bp gene, and was used as a homology plasmid to make a recombinant SPV, SVR12.

(2) Constructing pSP911-EssORF2 (FIG. 2)

The sequence between KpnI and PstI of pSP91 were replaced with the synthetic adapter shown in SEQ ID NO: 9 to insert the vaccinia virus 11-kD promoter into it. The resulting plasmid was designated as pSP911.

SEQ ID NO: 9:
GGTACCGAGCTCGGTAGCCCGGGCCATGGTAGATCCTCTAGAGGATCCAA
TTCATTTATAGCATAGAAAAAAACAAAATGAAATTCTACTATATTTTCTG
CAG

A synthetic nucleic acid sequence encoding a modified ORF2 of PCV2 (Ess_ORF2) was obtained by digesting pGTPs-Ess_ORF2 with BamHI and SalI, and inserted into the pSP911 cut with BamHI and SalI. The resulting plasmid was designated as pSP911-Ess_ORF2, and used for making recombinant swinepox viruses SVR13.

Example 2: Producing Recombinant Swinepox Viruses (rSPVs)

(1) Production of SVR12 (FIG. 3)

Recombinant SPV was generated in ESK-4 cells by homologous recombination between wild-type SPV genome and homology vectors. Sub-confluent ESK-4 cells in a 6-well plate were infected with wild-type SPV (wtSPV), and 17 hrs later the wtSPV-infected cells were transfection with 2 μg of pSP92-Ess_ORF2 using Lipofectamin Plus reagent (Invitrogen) and allowed to incubate at 37.0 for 5 days until cytopathic effect (CPE) had occurred. Cell lysates from infected-transfected cells were screened for recombinant plaques expressing β-galactosidase by the addition of 0.5 mg/ml Bluo-gal (Invitrogen Cat. No.: 15519-028) in the nutrient agarose overlay. Two independent wtSPV-free recombinant viruses were purified through 3-4 rounds of screening. The purified rSPV was designated as SVR12. Two purified clones of SVR12 were designated 1H2C9D4G5 and 2F5D5E5 clones.

(2) Production of SVR13 (FIG. 3)

Sub-confluent ESK-4 cells in a 6-well plate were infected with wild-type SPV (wtSPV), and 17 hrs later the wtSPV-infected cells were transfection with 2 μg of pSP911-Ess_ORF2 using Lipofectamin Plus reagent (Invitrogen) and allowed to incubate at 37.0 for until cytopathic effect (CPE) had occurred. Cell lysates from infected-transfected cells were transfection seed (TFS) for SVR13. TFS was diluted into 1:20 with Ham's F-12K medium without FBS, and infected into ESK-4 cells in 96-well plates. Seven days later, infected cells were lysed with lysis buffer (20 mM Tris-Cl, 0.1M NaCl, 5 mM EDTA, 0.1% SDS, 200 μg/ml protenase K) followed by heat treatment (60° C. 5 min, and 98° C. 2 min). These infected-cell-lysed DNA samples were screened by PCR with a primer set of 5'-GGCCGTTGA-TATGATGAGGT-3' (SEQ ID NO:10) and 5'-TCCAG-CACTGGCTTAGGAGT-3' (SEQ ID NO:11).

Samples amplifying 0.3 kbp DNA fragment were positive, and the corresponding supernatants were forwarded to the next step of screening. Screening was repeated until all appeared plaques were stained with immunofluorescence assay (IFA) using anti-PCV2 pig serum (PAB-PCV2, VMR) as the 1st antibody and FITC-conjugated anti-pig IgG (F1638-2ML, SIGMA) as the 2nd antibody.

Two wtSPV-free recombinant clones of SVR13 were purified from TFS through three rounds of screening, and designated as G2C2D4 and D10E5A5 clones.

Example 3: In Vitro Analysis of Recombinant SPVs (1) Expression of PCV2-ORF2 Genes by Western Blot Molecular sizes of PCV2-ORF2 proteins expressed by rSPVs were analyzed by a 15% SDS-PAGE and Western blot analysis using anti-PCV2 rat sera. ESK-4 cells were infected with SVR12 clone 1H2C9D4G5, clone 2F5D5E5, SVR14, SVR15 or wtSPV. Six days later, cell lysates were fractionated on a 15% SDS-PAGE. Proteins were transferred onto a polyvinylidene difluoride (PVDF) membrane, Immobilon-P (Merk Millipore, Cat. No.: IPVH08130), and blocked with 5% dried milk in PBS. PDVF membrane blots were probed with rat anti-PCV2 sera (1:1,000) as the 1st antibody, followed by reacting with biotin conjugated goat anti-rat IgG secondary (1:1,000), and VECTASTAIN ABC-AP Standard Kit (Vector Labs, AK-5000). Membrane blots were developed with alkaline phosphatase substrate, Nitroblue Tetrazolium (NBT)/5-Bromo-4-Chloro-3-Indolyl Phosphate (BCIP).

Results of western blotting showed that SVR12 and SVR13 expressed two kinds of ORF2, molecular sizes of 27 kDa and 25 kDa (FIG. 4). The former 27 kDa protein corresponds to a precursor form, and the latter 25 kDa corresponds to a processed form after cleavage at the end of the B5R signal peptide. These results thus demonstrate effective expression of antigens from the SPVs of the invention.

(2) Long-Term Stability and Expression of PCV2-ORF2 Gene

To check the stability of rSPVs of the invention using the IL-18bp gene as the insertion site, SVR12, and SVR13 were passed to ESK-4 cells 15 times. Stability and expression of inserted genes after ×15 passages were checked by PCR and western blotting. The results of PCR showed that inserted genes of all rSPVs were stable after 15× in vitro passages (FIG. 5). No band of irregular sizes of PCV2-ORF2 gene products appeared in the lanes of ×15 in vitro passages on the PDVF membrane compared to that of ×0 passage by western blot analysis.

(3) Growth of Recombinants in Non-Target Animal Cells

Safety into environment of a genetically engineered live vaccine is an important concern. As a safety risk assessment of SPVs, the infectivity or growth ability in non-target animal or cell lines can be tested. SPVs generally do not growth in HeLa cells, but can grow in Vero cells. Vero cells have been extensively tested and shown to be free from adventitious agents, and are the most widely accepted by regulatory authorities to use for vaccine production such as polio and porcine epidemic diarrhea vaccines.

Vero cells (ATCC CCL-81; commercial cell line derived from the kidney of an African green monkey) cultivated in 6-well plates were infected in separate cultures with three SPVs: SVR12 and two comparative SPVs, namely SVR3, which comprises an ORF2 gene in ARP cloning site, and SVR7, which comprises an ORF2 gene in TK cloning site. Infection was performed at two multiplicity of infection (MOI) (High: ~0.01, and Low: ~0.001), and the cells were cultivated in 37° C. incubator with 5% $CO_2$ for two weeks after infection. At 0, 4, 7, 11 and 14 days post infection (DPI), infected cells and supernatants were recovered, freeze and thawed. Infectious virus amounts at 0, 4, 7, 11 and 14 DPI were titrated by $TCID_{50}$ assay using ESK-4 cells in 24-well plates.

The results are summarized in Table 1 and FIG. 6. Relative growth ratios to each titer of '0 DPI' are shown in parentheses in Table 1, and the time course of the relative growth ratios are plotted in FIG. 6. The results surprisingly show that the growth ability of recombinant SPVs is influenced by the insertion sites, and that recombinant SPVs of the invention, using the IL-18bp gene as the insertion site, advantageously did not grow in Vero cells.

This is a further advantage of the recombinant SPVs of the invention using IL-18bp gene as the insertion site on the point of lower risk to the environment.

TABLE 1

Growth of rSPVs in Vero cells

| Virus | MOI | Virus Titer: TCID50/well (Ratio to 0 DPI) | | | | |
|---|---|---|---|---|---|---|
| | | 0 DPI | 4 DPI | 7 DPI | 11 DPI | 14 DPI |
| SVR 3 | High | 4.8E+04 (1.0) | 6.3E+05 (13.1) | 8.5E+05 (17.7) | 6.3E+05 (13.1) | 4.2E+05 (8.7) |
| | Low | 4.8E+03 (1.0) | 8.5E+04 (17.7) | 1.4E+05 (29.2) | 8.5E+04 (17.7) | 6.3E+04 (13.1) |
| SVR 7 | High | 4.8E+04 (1.0) | 4.2E+05 (8.8) | 4.2E+05 (8.8) | 1.4E+05 (2.8) | 1.4E+05 (2.8) |
| | Low | 4.8E+03 (1.0) | 4.8E+04 (10.0) | 8.5E+04 (17.8) | 6.3E+04 (13.1) | 1.4E+04 (2.8) |
| SVR 12 | High | 8.5E+03 (1.0) | 4.8E+03 (056) | 4.2E+03 (0.49) | 85E+02 (0.10) | 1.4E+02 (0.02) |
| | Low | 8.5E+02 (1.0) | 4.2E+02 (049) | 1.4E+02 (0.16) | 8.5E+01 (0.10) | 6.3E+01 (007) |

Example 4: Induction of an Immune Response In Vivo

Groups (N=7) of anti-PCV2 antibody-negative 4-week-old piglets were immunized subcutaneously in the left ear lobe with each of recombinant SPVs, SVR7 or SVR12 at 5.0E+04 TCID$_{50}$/pig, or with PBS. Blood samples were taken from external jugular vein at pre-immune, 1, 2 and 3 weeks post immunization (wpi), and anti-PCV2 antibody in sera were measured by indirect immunofluorescence. PCV2-infected RPL-2 cells were cultivated on 96-well tissue culture plates, and fixed by acetone/methanol (2:1). After blocking with 0.5% Non-Fat milk in PBS for 1 hour, the two fold dilutions of the sera were layered onto the 96-well tissue culture plate wells and incubated for 1 hour at 37° C. Serially diluted PAB-PCV2 (VMRD) pig sera were also layered on one lane of each 96-well plate as positive control sera. After incubation, the plates were washed 3 times and anti-pig IgG-FITC antibodies produced in rabbit (SIGMA Cat. #: F1638, 1:1000) were layered onto the 96-well tissue culture plate wells and incubated for 1 hour at 37° C. After incubation, the plates were washed with PBS three times. Signals of the secondary antibodies were detected by a fluorescent microscopy, and positive or negative signal of each well was recorded. The highest dilution resulting in a positive fluorescent reaction was the IF titer of the sample, and experimental errors among plates and days were calibrated by the IF titer (1:2560) of the positive control sera.

The results obtained show that average IF titers of SVR12-vaccinated group were statistically ($p<0.05$) higher than that of SVR7-vaccinated group. Furthermore, clinical observation of formed pock or redness at the vaccination sites was started from 1 to 3 wpi. The peak pock sizes of SVR12-vaccinated group were smaller than those of SVR7-vaccinated group.

The above results indicate that rSPV of the invention in which a foreign gene is inserted within the IL-18bp gene, such as SVR12, was more attenuated, and could induce higher immune-responses than rSPV using TK site as the insertion site such as SVR7.

The invention claimed is:

1. A recombinant swinepox virus (rSPV) comprising at least one first foreign gene sequence in its genome, wherein said first foreign gene sequence is inserted into the IL-18 binding protein (IL18 bp) gene of the rSPV genome.

2. The rSPV of claim 1, wherein the first foreign gene sequence is inserted in replacement of all or a portion of the viral IL18 bp gene sequence.

3. The rSPV of claim 2, wherein the rSPV genome comprises a deletion of at least 100 bp of the IL18 bp gene sequence, and wherein the first foreign gene sequence is located in said deletion.

4. The rSPV of claim 1, further comprising at least a second foreign gene sequence inserted in a distinct region of the rSPV genome.

5. The rSPV of claim 1, wherein the first and/or second foreign gene sequences encode an antigen.

6. The rSPV of claim 1, wherein the first or second foreign gene sequences encode a PCV2 capsid antigen.

7. The rSPV of claim 1, wherein each of the first and/or second foreign gene sequences contains a transcriptional promoter.

8. The rSPV of claim 7, wherein the promoter is selected from the vaccinia virus 7.5-kD promoter (P7.5k), 11-kD promoter (P11k), or 28-kD promoter (P28k), an artificial synthetic Poxvirus promoter (Ps), the chicken beta-actin (Bac) promoter or a derivative thereof, the Pec promoter, the Murine Cytomegalovirus (Mcmv) immediate-early (ie)1 promoter, the Human Cytomegalovirus promoter (Hcmv), the Simian virus (SV)40 promoter, and the Raus Sarcoma virus (RSV) promoter, or any fragments thereof which retain a promoter activity.

9. A rSPV of claim 1, comprising a nucleic acid sequence encoding a PCV2 antigen in its genome, wherein said nucleic acid sequence is inserted into the IL18 bp gene of the rSPV genome.

10. A nucleic acid molecule comprising the genome of a rSPV of claim 1.

11. A host cell comprising a rSPV of claim 1 or a nucleic acid molecule of claim 10.

12. A method for producing a rSVP of claim 1, comprising infecting a competent cell with a nucleic acid molecule of claim 10 and collecting the rSVP.

13. A composition comprising a rSVP of claim 1 and an excipient.

14. A composition of claim 13, which is a vaccine.

15. A method for immunizing a porcine against a pathogen comprising administering to said porcine a rSPV of claim 1.

16. A vaccination kit for immunizing a porcine which comprises the following components:
a. an effective amount of a vaccine of claim 14, and
b. a means for administering said vaccine to said porcine.

17. The rSPV of claim 4, wherein the second foreign gene sequence is inserted into the viral Thymidine kinase (TK) gene or Ankyrin repeat protein gene.

18. The rSPV of claim 5, wherein the first and/or second foreign gene sequences encode a Porcine Circovirus type 2 (PCV2) antigen.

19. The rSPV of claim 6, wherein the first or second foreign gene sequences encode a PCV2 ORF2 protein or peptide.

20. The rSPV of claim 4, wherein the first and/or second foreign gene sequences encode an antigen.

21. The rSPV of claim 4, wherein the first or second foreign gene sequences encode a PCV2 capsid antigen.

22. The rSPV of claim 4, wherein each of the first and/or second foreign gene sequences contains a transcriptional promoter.

* * * * *

SEQUENCE LISTING

<160> NUMBER OF SEQ ID NOS: 11

<210> SEQ ID NO 1
<211> LENGTH: 22
<212> TYPE: DNA
<213> ORGANISM: Artificial sequence
<220> FEATURE:
<223> OTHER INFORMATION: oligonucleotide

<400> SEQUENCE: 1
cgaattcatt cctttatctt ta                                          22

<210> SEQ ID NO 2
<211> LENGTH: 21
<212> TYPE: DNA
<213> ORGANISM: Artificial sequence
<220> FEATURE:
<223> OTHER INFORMATION: oligonucleotide

<400> SEQUENCE: 2
ggaactacgt tatacgatca t                                           21

<210> SEQ ID NO 3
<211> LENGTH: 38
<212> TYPE: DNA
<213> ORGANISM: Artificial sequence
<220> FEATURE:
<223> OTHER INFORMATION: oligonucleotide

<400> SEQUENCE: 3 ttcgcccttacggtaccattcctttatctttataaacg 38

<210> SEQ ID NO 4
<211> LENGTH: 39
<212> TYPE: DNA
<213> ORGANISM: Artificial sequence
<220> FEATURE:
<223> OTHER INFORMATION: oligonucleotide

<400> SEQUENCE: 4
ctataatatt aaataagctt tatggagttg tttaaatac 39

<210> SEQ ID NO 5
<211> LENGTH: 35
<212> TYPE: DNA
<213> ORGANISM: Artificial sequence
<220> FEATURE:
<223> OTHER INFORMATION: oligonucleotide

<400> SEQUENCE: 5
cacacgataa cactgcagtc cacatattac ggttc 35

<210> SEQ ID NO 6
<211> LENGTH: 32
<212> TYPE: DNA
<213> ORGANISM: Artificial sequence
<220> FEATURE:
<223> OTHER INFORMATION: oligonucleotide

<400> SEQUENCE: 6
gccgcgaatt cgccctcgag gagctcacta cg 32

<210> SEQ ID NO 7
<211> LENGTH: 46
<212> TYPE: DNA
<213> ORGANISM: Artificial sequence
<220> FEATURE:
<223> OTHER INFORMATION: oligonucleotide

<400> SEQUENCE: 7
aattgcccgg gtaccgtcga tcgactttttt atggcccccc cggcca 46

<210> SEQ ID NO 8
<211> LENGTH: 46
<212> TYPE: DNA
<213> ORGANISM: Artificial sequence
<220> FEATURE:
<223> OTHER INFORMATION: oligonucleotide

<400> SEQUENCE: 8
agcttggccg ggggggccat aaaaagtcga tcgacggtac ccgggc 46

<210> SEQ ID NO 9
<211> LENGTH: 103
<212> TYPE: DNA
<213> ORGANISM: Artificial sequence
<220> FEATURE:
<223> OTHER INFORMATION: P11K promoter

<400> SEQUENCE: 9
ggtaccgagc tcggtagccc gggccatggt agatcctcta gaggatccaa ttcatttata 60
gcatagaaaa aaacaaaatg aaattctact atattttctg cag 103

<210> SEQ ID NO 10
<211> LENGTH: 20

```
<212> TYPE: DNA
<213> ORGANISM: Artificial sequence
<220> FEATURE:
<223> OTHER INFORMATION: oligonucleotide

<400> SEQUENCE: 10
ggccgttgat atgatgaggt                                          20

<210> SEQ ID NO 11
<211> LENGTH: 20
<212> TYPE: DNA
<213> ORGANISM: Artificial sequence
<220> FEATURE:
<223> OTHER INFORMATION: oligonucleotide

<400> SEQUENCE: 11
tccagcactg gcttaggagt                                          20
```